United States Patent [19]

Dahms

[11] Patent Number: 4,808,646
[45] Date of Patent: Feb. 28, 1989

[54] MALEIMIDE-MALEAMIC ACID RESIN SOLUTION

[75] Inventor: Ronald H. Dahms, Springfield, Mass.

[73] Assignee: Monsanto Company, St. Louis, Mo.

[21] Appl. No.: 62,805

[22] Filed: Jun. 15, 1987

Related U.S. Application Data

[63] Continuation-in-part of Ser. No. 944,158, Dec. 18, 1986.

[51] Int. Cl.$^4$ .......................................... C08F 226/06
[52] U.S. Cl. .................. 524/104; 428/473.5; 428/500; 524/111; 524/173; 524/233; 524/548; 524/606; 528/170; 528/220; 528/229; 528/321; 528/322; 548/522; 548/548
[58] Field of Search .............. 528/322, 321, 170, 220, 528/229; 524/606, 173, 233, 111, 104, 548; 526/262

[56] References Cited

U.S. PATENT DOCUMENTS

| | | | |
|---|---|---|---|
| 3,839,358 | 10/1974 | Bargain | 260/326.26 |
| 3,975,401 | 10/1976 | Balme | 260/326.26 |
| 4,130,564 | 12/1978 | Haug et al. | 260/326.26 |
| 4,460,783 | 7/1984 | Nishikawa et al. | 548/549 |
| 4,582,883 | 4/1986 | de Koning et al. | 526/262 |
| 4,654,407 | 3/1987 | Domeier | 526/262 |

FOREIGN PATENT DOCUMENTS 1374127 11/1971 United Kingdom .

OTHER PUBLICATIONS

Harvey et al., "New Aromatic-Ether Bismaleimide Matrix Resins", ANTEC '86, p. 1311.

Primary Examiner—Harold D. Anderson
Attorney, Agent, or Firm—William J. Farrington; Thomas E. Kelley

[57] ABSTRACT

Solutions of maleimide resins comprising a mixture of bismaleimides and low but solubilizing amounts of maleamic acids are provided at high solids levels, e.g. at least about 50%. Such solutions which comprise common solvents such as acetone, methyl ethyl ketone and toluene are useful in preparing laminates based on bismaleimide resins.

11 Claims, No Drawings

MALEIMIDE-MALEAMIC ACID RESIN SOLUTION

This application is a continuation-in-part of copending application Ser. No. 944,158, filed Dec. 18, 1986, incorporated herein by reference.

Disclosed herein are soluble compositions of mixtures of maleimide and maleamic acid compounds, solutions of such mixtures, laminates based on such compositions as well as methods of making and using such compositions, solutions and laminates.

BACKGROUND OF THE INVENTION

Bisimide resins, e.g. bismaleimide resins, are advantageously used in providing resin matrix composites, e.g. glass or carbon fiber reinforced laminates, to achieve enhanced properties such as greater thermal stability and lower moisture sensitivity than is possible with other composites, e.g. composites based on epoxy or other resins. A common bisimide, i.e. bis(4-maleimidophenyl)methane, exhibits poor solubility in many organic solvents of choice. Its use in commercial manufacture of laminates is facilitated by dissolving the bisimide in N-methyl pyrrolidone (not a preferred solvent) and by chain extension by Michael addition reaction with diamines.

Nishikawa, et al., disclose in U.S. Pat. No. 4,460,783 that certain aromatic ether bismaleimide compounds such as bis(maleimidophenoxyphenyl) propane and the like are highly soluble in desirable solvents such as acetone, toluene, methyl ethyl ketone and the like. See also Harvey et al in "New Aromatic-Ether Bismaleimide Matrix Resins", *ANTEC '86*, page 1311. It has been discovered that in their purer forms such aromatic ether bismaleimides have low solubility. It has been further discovered that the solubility of such aromatic ether bismaleimides, as well as other bismaleimides generally, can be enhanced by the presence of a solubilizing amount of compounds having at least one terminal maleamic acid group. Bisimide resins have been preferably prepared with low levels (if any) of terminal maleamic acid groups which tend to liberate water from ring closing imidization during cure of such resin. Such water can vaporize at commonly used fabrication temperatures, tending to generate voids or blisters in fabricated articles such as laminates. For instance, Bargain in U.S. Pat. No. 3,839,358 discloses that bismaleimides, e.g. bis(4-maleimidophenyl)methane, are prepared by reacting a diamine with maleic anhydride followed by catalytic cyclodehydration. The bismaleimide is purified, i.e. separated from acid-containing species, by washing with a basic solution, e.g. aqueous sodium bicarbonate. See also Balme who discloses in U.S. Pat. No. 3,975,401 a method for reducing the proportion of maleimido-acid (i.e. maleamic acid) groups in the precipitated product of cyclodehydration.

Although such acid groups can liberate water during cure conditions, it has been discoverd that low amounts of liberated water can be tolerated in many fabrication practices. However, in critical applications it is especially desirable that bisimide resins cure with minimal liberation of water, e.g. to avoid blisters that can form when laminates of the cured bisimide resin are subjected to high temperatures, e.g. as in vapor phase soldering.

An object of this invention is to provide soluble bismaleimide resin comprising predominately bismaleimides and low but solubilizing amounts of maleamic acids.

Another object is to provide concentrated solutions of such resins in common organic solvents. Yet another object is to provide such solutions with desirably long stability, for instance, for days, weeks or even longer.

Still another object is to provide laminates, and methods of making laminates, from such resins, especially from solutions that rapidly form a viscous thermoplastic resin that allows for minimal resin flow from reinforced matrices even during severe curing conditions, e.g. high pressure.

These and other objects of this invention are possible since it has been discovered that the addition of minor amounts of maleamic acids can greatly enhance the solubility of bismaleimides in common organic solvents, affording greatly enhanced utility in fabrication, e.g. of laminates, without substantially deleterious effects of liberated water.

SUMMARY OF THE INVENTION

This invention provides methods of preparing highly soluble bismaleimidme compositions by providing mixtures of such bismaleides and solubilizing amounts of maleamic acids. This invention also provides such soluble compositions, solutions thereof as well as methods of using such compositions and solutions to prepare laminates. Such compositions, and solutions thereof, are devoid of other carboxylic acids and anhydrides, e.g. acetic acid and/or acetic anhydride which are commonly used as dehydrating agents in the preparation of such mixtures.

DETAILED DESCRIPTION OF THE INVENTION

The methods of preparing highly soluble bismaleimide compositions according to this invention comprise providing a mixture of bismaleimide and a solubilizing amount of maleamic acids. Such bismaleimide compositions are soluble in a variety of common organic solvents and are conveniently characterized as being acetone-soluble as distinguished from the pure forms of most bismaleimides which exhibit low, e.g. about 5 weight percent, solubility in acetone at about room temperature.

The methods of this invention can be employed with any of the bismaleimides and maleamic acids of the formula:

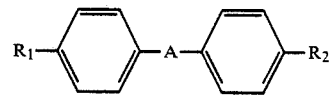

where A is —B—,

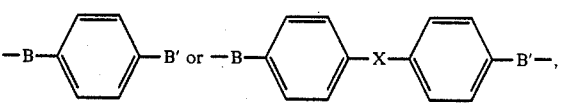

where B,B' and X are independently —O—, —SO—, —CO—, or

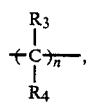

$R_3$ and $R_4$ being independently hydrogen, $C_1$-$C_3$ alkyl, and halogenated $C_1$-$C_3$ alkyl and n ranging from 0 to 6, where $R_1$ and $R_2$ are independently the maleamic acid group, —NHCOCH=CHCOOH, or the maleimide group,

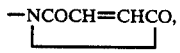

wherein $R_1$ and $R_2$ are the same providing a mixture of bismaleimide and bismaleamic acid and are different thereby providing a maleimide-maleamic acid. As used herein the term maleamic acids includes bismaleamic acids and half imidized intermediate referred to as a maleimide-maleamic acid.

In certain preferred embodiments of this invention the mixture comprises maleimides derived from bis-(aminophenoxyphenyl) propane, i.e. A is

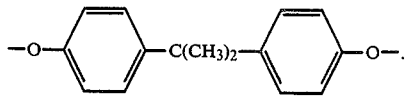

In other preferred embodiments of this invention the mixture comprises maleimides derived from bis-(aminophenyl) methane.

Although purified bismaleimides and bismaleamic acids generally tend to be insoluble in common organic solvents such as acetone, methyl ethyl ketone and toluene, compositions comprising mixtures of bismaleimides and maleamic acids as specified above have been found to be surprisingly soluble in such solvents. Accordingly, this invention also provides novel and useful, highly soluble mixtures of bismaleimides and maleamic acids.

Such mixtures of maleimides and maleamic acids can be prepared from diamine precursors by methods generally known in the art and disclosed, for instance, in U.S. Pat. Nos. 3,562,223 and 4,460,783, both of which are incorporated herein by reference. The mixtures of bismaleimides and maleamic acids which desirably are predominately bismaleimides with lesser amounts of maleamic acids, e.g. residual bismaleamic acid, can be prepared by ring closure imidization of the bismaleamic acid precursor.

Bismaleamic acid can generally be obtained in substantially pure quantities, e.g. at least about 90% bismaleamic acid or higher, say at least about 98% purity, by condensation reaction, e.g. in a liquid medium such as acetone, of maleic anhydride with a diamine of the formula

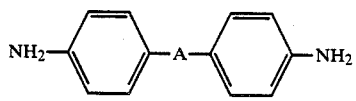

where A is as defined above. The maleimides can be formed from the bismaleamic acid precursor, e.g. suspended in a liquid medium such as acetone, by ring closure imidization resulting in the liberation of water.

This ring closure is desirably effected in the presence of an acid anhydride dehydrating agent such as acetic anhydride, a tertiary amine ring closing agent such as triethylamine, and a metal acetate catalyst such as ferrous acetate, nickel acetate or preferably, for more complete imidization, cobalt acetate. The ring closing reaction is readily carried out at the reflux temperature of the liquid medium to provide a solution comprising predominately the bismaleimide and maleamic acids, i.e. residual bismaleamic acid precursor and the half-imidized intermediate. Quenching the solution in cold water produces a precipitate mixture of bismaleimide and maleamic acids. The mixture can be made to be substantially devoid of other carboxylic acid, e.g. which may be occluded acid which was formed from the acid anhydride dehydrating agent, by washing and/or recrystallization. Such washing, e.g. with water, should be with an acidic or at least neutral liquid to avoid excessive solubilization of the maleamic acids as may occur when basic liquids are used. When washing with basic liquids is desired, contact time should be short to avoid excessive solubilization of maleamic acids. Such recrystallization may be effected from any common organic solvent, e.g. acetone, methyl ethyl ketone, toluene and the like.

Acetone-soluble mixtures of bismaleimides and maleamic acids can comprise about 40 to about 95 parts by weight bismaleimide; the remainder of 100 parts by weight of such mixture will generally comprise maleamic acids, i.e. residual bismaleamic acid and the half-imidized intermediate. More preferably, such mixtures will comprise at least about 50 or 60 and up to about 85 or at least 80 parts by weight of the bismaleimide. In many cases the amount of bismaleamic acid will be from about 1 to less than about 30 parts by weight, preferably often less than about 10 parts.

The amount of such maleamic acids is conveniently expressed in terms of "acidity" based on maleamic acid groups as a percent of total acidity when all of the maleimide and maleamic acid groups are taken as maleamic acid groups. When the mixture is prepared from a known amount of bismaleamic acid precursor, such acidity is readily determined by titrating a sample of the mixture to a neutral end-point with a standard base, e.g. N/20 KOH; acidity is determined with reference to the titer of the bismaleamic acid precursor.

Preferably, the ring closing reaction is carried out so that the acidity is less than about 40% and under conditions mild enough to prevent the formation of substantial amounts of higher molecular weight oligomers. More preferably, acidity will be in the range of about 1-20%. In many cases where it is desirable to provide a highly soluble maleimide that liberates low amounts of water upon curing, it is most preferred that acidity be in the range of about 2-15%, e.g. about 3-12%.

This invention also provides solutions of highly soluble mixtures of bismaleimides in common organic solvents such as acetone, methyl ethyl ketone and toluene, or mixtures thereof. Such solutions can be provided by solvents selected from the group consisting not only of acetone, methyl ethyl ketone, and toluene but also of methyl isobutyl ketone, tetrahydrofuran, dimethylformamide, dimethylacetamide, dimethylsulfoxide, N-methyl pyrrolidone, ethylene dichloride, and xylene and the like or a mixture of such solvents. In many cases, the solvent of choice will consist essentially of acetone.

Solutions of bismaleimide resin of this invention are useful in providing matrix composites and often desirably comprise from about 40 to about 90 percent solids of resin mixtures of bismaleimide and maleamic acid. Useful resin solutions will generally have a viscosity between 50 and 500 centipoise, although process requirements may require viscosities outside of that range. In many cases it is especially desirable that such solutions have a viscosity between about 100 and 200 centipoise.

When solutions are intended to be used within a short period of time (e.g. within minutes or even hours, of dissolution) solutions of such mixtures, of at least about 50% by weight or higher, e.g. about 70%, can be obtained. However, in many cases, especially with relatively high concentrations of such mixtures, e.g. at least about 50% by weight, the bismaleimide component of the solution tends to separate over time from the solution in substantial quantities resulting in a solution containing disproportionately higher amounts of resin having maleamic acid terminal groups. Such maleamic acid terminal groups often undergo ring closing during cure with the result of liberation of water which may undesirably tend to form voids or blisters in composites.

It has been discovered that separation of bismaleimide compounds from solutions can be avoided by providing in the solutions of such mixtures of maleimides and maleamic acid a minor amount of a species capable of interacting with maleamic acid groups to form amides, esters, etc., or with terminal unsaturation. Such species can comprise amines, e.g. polyamines. The amount of polyamine present in the solution to provide stability can be conveniently expressed in terms of equivalents of amine groups and maleamic acid groups, e.g. conveniently expressed in terms of the ratio of amine groups to maleamic acid groups. When the polyamine is present in solution such that the amount of amine groups is substantially less than the equivalent amount of maleamic acid groups, solubility may be enhanced but for a shorter period of time than when substantially the equivalent amounts are utilized. Moreover, when the polyamine is present such that the amount of amine groups is substantially greater than the equivalent amount of maleamic acid groups, stability will generally tend to be lessened, often with substantially increased viscosity of the solution. Such viscous solutions may tend to gel rapidly on heating, providing undesirable resin composites.

Considerable latitude can often be employed in determining such equivalence. In many cases it is advantageous to provide solutions where the ratio of amine groups to maleamic acid groups is from about 0.5 to about 4. To achieve exceptionally long stability, e.g. for days or weeks or more, without separation, e.g. by precipitation of a maleimide or maleamic acid component of the mixture, and to prevent an undue increase in viscosity, it is generally useful to provide polyamine so that the amount of amine groups is more nearly the equivalent of maleamic acid groups, e.g. where the ratio of amine groups to maleamic acid groups is about 0.8 to 2, and most preferably about 0.9 to 1.5.

The polyamine can comprise a diamine as used in preparing the bismaleimides of this invention, i.e. a diamine of the formula

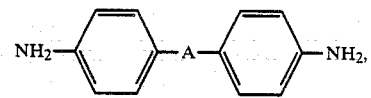

where A is described above or where the rings are saturated. Alternatively, the polyamine can be another diamine such as alkyl diamine, for instance diaminopropane, putrescine, cadaverine, hexamethylene diamine, and the like, or a triamine such as triaminononane and the like. It has been found that stable solutions that allow the resin to rapidly become viscous upon heating are achievable when the polyamine contains secondary amines, such as diethylenetriamine, triethylenetetramine, tetraethylenepentamine, pentaethylenehexamine, and polyethyleneimine. Especially desirable resins that become rapidly viscous upon heating are provided with polyamines containing at least two secondary amines.

In one method of forming resin matrix composites, cloth-like layers such as glass or carbon fiber cloth (woven or non-woven) is saturated with a solution of this invention. Such saturation can be conveniently carried out by dipping such cloth into a resin solution. Excess solution can be removed by passing the cloth through squeeze rolls. Solvent is removed in any convenient manner such as by heating the solution-saturated cloth, e.g. in an oven at a temperature oftnn above the boiling point of the solvent. The length of time at elevated temperature is desirably short, e.g. less than about 10 minutes, but will be sufficiently long to remove solvent and promote partial reaction of the resin to a coherent thermoplastic state (often called B-staging) providing a dry (e.g. solventless but often tacky) resin-impregnated cloth, commonly called a "pre-preg". Such resin-impregnated cloth can then be provided in one or more layers which can be thermoformed, e.g. heated in a compressed stack and cured to provide a laminate by heating for an extended period of time, e.g. about an hour or more, at elevated temperatures say between about 150° and 300° C., preferably at least about 180° C. to about 250° C.

An effective amount of polyamine will also facilitate formation of dry resin-impregnated cloth. With low levels of polyamine, the resin will often remain molten, e.g. at temperatures of about 200° C., for undesirably long times, e.g. 20 minutes or more, even hours without reacting sufficiently to form a dry thermoplastic resin. When high levels of polyamine are utilized, e.g. substantially higher than about the equivalent amount of maleamic acid, the resin generally tends to rapidly gel upon heating, providing an undesirable foamy, brittle resin. Desirably the polyamine will assist in providing such dry thermoplastic resin in a short time, say less than about 10 minutes, preferably on the order of about 1 to 2 minutes. The time for formation of such dry thermoplastic resin is often correlated with "Dry Rubber Time", a predictive test defined more particularly herein in Example 4.

Some polyamines, e.g. diamines, allow for advantageous Dry Rubber Times, e.g. about 3 minutes or less, for solutions that are maintained for a short period of time, say about a day or so. However, when such solutions are maintained for longer times, e.g. about a week or more, Dry Rubber Times tend to increase to undesirable levels, e.g. about 5 minutes to 20 minutes or more. Advantageously, polyamines having secondary amine groups allow for short Dry Rubber Times even when solutions are maintained for several weeks. Accordingly, preferred aspects of the inventions disclosed herein comprise polyamines having secondary amine groups.

The solutions of this invention may also comprise a variety of other materials that can be useful in providing laminates with desirable properties. Such materials may include fillers, such as silica, thermoplastics and/or reactants having one or more vinyl, epoxy, or cyanate ester groups, as illustrated in U.S. Pat. No. 4,654,407, incorporated herein by reference.

The following disclosure is provided to illustrate specific embodiments and aspects of the invention but does not imply any limitation of the scope of the invention.

EXAMPLE 1

This example serves to illustrate the preparation of a soluble mixture of bismaleimides and maleamic acids derived from bis(aminophenoxyphenyl) propane and its use in preparing solutions according to this invention.

351 grams of maleic anhydride and 1,012 grams of acetone were heated to reflux temperature (about 63° C.) in a 5-liter reaction flask. A solution of 693 grams of 2,2-bis[4-(4-amino-phenoxy)phenyl]propane in 1,350 grams of acetone was metered into the refluxing solution over a period of 40 minutes. The reaction mixture was held at 30 minutes at reflux temperature to provide essentially 100 percent complete conversion to the bismaleamic acid of 2,2-bis[4-(4-amino-phenoxy)phenyl]-propane which precipitated as a yellow powder.

The following materials were added to the suspension of bismaleamic acid in refluxing acetone: 495 grams of acetic anhydride, 3.375 grams of nickel acetate tetrahydrate, and 58.5 grams of triethylamine. The suspension was maintained at reflux temperature for about two hours then cooled to 50° C. The resulting clear solution was stirred into cold water yielding a precipitated yellow powder which was washed with water to remove solubles, filtered and dried in an air oven at 60° C. to constant weight. Analysis by high pressure liquid chromatography indicated that the powder comprised about 76 percent of the bismaleimide of 2,2-bis[4-(4-aminophenoxy)phenyl]propane and about 5 percent of the precursor bismaleamic acid; the balance of the powder is believed to be the half-imidized intermediate having both maleimide and maleamic acid terminal groups. The powder was dissolved in acetone from 40 to about 60 percent by weight to provide solutions according to this invention.

EXAMPLE 2

This example serves to illustrate the preparation of a soluble mixture of bismaleimides and maleamic acids derived from methylene dianiline and its use in preparing solutions according to this invention.

39.6 grams of methylene dianiline, 1.5 grams of benzyl dimethylamine, and 150 grams of acetone were cooled in a 500 cc flask to about 4° C. A solution of 43.1 grams of maleic anhydride in 200 grams of acetone was added over about a one hour period. The bismaleamic acid of methylene dianiline formed as a yellow precipitate as the mixture was stirred for an additional two hours at about 4° C. The bismaleamic acid was filtered, rinsed with acetone and dried at 65° C.

78.8 grams of the bismaleamic acid, 330 grams of acetic anhydride, 3.5 grams of calcium acetate monohydrate, and 400 grams of acetone were heated in a 1-liter flask for about one hour at reflux (about 60° C.). Acetone was evaporated until the temperature rose to about 80° C. After continuing refluxing at about 80° C. for about 2 hours, the reaction mixture was poured into water resulting in a precipitate which was washed in water and filtered. Analysis by high pressure liquid chromatography indicated that the precipitate comprised about 49% of bismaleimide of methylene dianiline and about 34% of bismaleamic acid of methylene dianiline; the balance of the precipitate is believed to be the intermediate product having both maleimide and maleamic acid terminal groups.

A portion of the mixture was dried for one minute on a hot plate (about 167° C.) and dissolved in acetone to provide a solution according to this invention comprising about 50% solids. After several days a small amount of acetone insoluble material precipitated from the 50% solution.

Another solution according to this invention (about 75% solids in acetone) exhibited less stability with substantial amounts of acetone insoluble precipitate forming after about several hours.

The surprising solubility of a mixture of bismaleimide and maleamic acids derived from methylene dianiline is further indicated by comparison of solubilities of pure materials. As indicated above in the description of the formation, the solubility of the bismaleamic acid in acetone is extremely low. Moreover, commercially available bismaleimide of methylene dianiline (from Aldrich Chemical Company, purity 85%) has a solubility in acetone of less than about 10%.

EXAMPLE 3

This example serves to illustrate methods of this invention in providing bismaleimides with solubilizing amounts of maleamic acids.

Bismaleimide of 2,2-bis[4-(4-aminophenoxy)phenyl]-propane was prepared essentially as in Example 1 except that the nickel acetate tetrahydrate was replaced with 0.32 g of each of the following cyclodehydration catalysts: cobalt acetate tetrahydrate, nickel acetate tetrahydrate, ferrous acetate, cupric acetate monohydrate, calcium acetate monohydrate, zinc acetate dihydrate, chromium triacetate monohydrate and sodium acetate. The results of the following analyses of the resultant yellow powder are reported in Table 1:

(a) the composition as determined by high pressure liquid chromatography (HPLC) in terms of the area ratios of bismaleimide, what is believed to be the half imidized intermediate and residual bismaleamic acid;

(b) the "acidity" as determined by titration and reported as a percent of the total acidity of the precursor bismaleamic acid; and (c) the room temperature solubility in acetone in weight percent.

The results reported in Table 1 indicate that high solubility of bismaleimides is highly dependent on the amount of solubilizing maleamic acid and that practice of preferred embodiments of this invention can be facilitated by use of a cobalt, nickel or ferrous acetate as a cyclodehydration catalyst in the preparation of bismaleimide.

TABLE 1

| Catalyst (cation) | Powder Composition[1] (BMI/MIMA/BMA) | Acidity % | Solubility |
|---|---|---|---|
| Co | 78/15/2 | 3 | >70% |
| Ni | 72/14/6 | 6 | >70% |
| Fe | 62/27/6 | 12 | >70% |
| Cu | 32/21/31 | 23 | <40% |
| Ca | 30/28/30 | 35 | <40% |
| Zn | 30/18/33 | 30 | <40% |
| Cr | 27/27/36 | 37 | <40% |
| Na | 43/33/13 | — | — |

[1]Reported in terms of HIPLC area ratios of principal components (i.e. bismaleimide (BMI), maleimide-maleamic acid (MIMA), and bismaleamic acid (BMA).

EXAMPLE 4

This example serves to illustrate the stabilizing effect of polyamines on solutions of mixtures of bismaleimides and maleamic acids and the effect of polyamines on curing of such resins as indicated by Dry Rubber Time. Dry Rubber Time provides an indication of relative cure rate especially for B-staging and, as specified herein, is a measurement of the time for a sample of resin solution to cure to a dry rubbery mass on a uniformly heated surface. More specifically, about a 1 cc sample of resin (dry or solution) is placed on a 200° C., uniformly-heated cure plate (Thermo-Electric Company, Cleveland, Ohio). The solvent rapidly evaporates as the solution is continuously spread with a spatula forming a molten resin. As the resin reacts to form polymer, thin strings can be pulled from the resin mass by the spatula. As the reaction continues, the resin mass forms into a coherent dry rubbery mass from which polymer strings cannot be drawn. The time at which strings are no longer formed is the "Dry Rubber Time". A Dry Rubber Time of "0" indicates almost immediate gelation of the solution.

The Dry Rubber Time for the resin mixture of bismaleimide and maleamic acids prepared in Example 1 was determined to be greater than three hours (about 10,000 seconds). That is, the test was discontinued after three hours when molten resin (at 200° C.) failed to form a coherent rubbery mass.

The addition of polyamine to a solution of such mixture provided substantially short Dry Rubber Times. Acetone solutions (about 60% solids) of the resin mixture of bismaleimides and maleamic acids and various polyamines were prepared as indicated in Table 1 by first dissolving the polyamine in acetone, then adding the resin mixture with agitation. The amount of polyamine is indicated by the ratio of amine groups to acid groups. For instance, the mixture of Example 1 was determined by titration to have 0.0362 equivalents of acid groups per 100 grams; and diaminoethane has 0.0333 equivaents of amine groups per gram (determined by dividing the number of amine groups, i.e. "2", by the molecular weight, i.e. "60"). Thus, adding 100 grams of the resin of Example 1 to a solution containing 0.94 grams of diaminoethane provides a solution where the ratio of amine groups to acid groups is determined to be about 0.86.

The results indicated in Table 2 indicate that polyamine can be advantageously added to solutions of soluble resin mixtures of bismaleimides and maleamic acids to provide exceptionally long stabiliy of such solutions, e.g. up to three weeks and longer. Moreover the results indicate that certain polyamines can provide exceptionally low Dry Rubber Times, e.g. often less than about 5 minutes less, even after three weeks of storage.

TABLE 2

| | | Dry Rubber Time (seconds) | | | |
|---|---|---|---|---|---|
| Polyamine | R* | As made | 1 day | 6 days | 3 weeks |
| Control-No amine | — | >10,000 | — | — | — |
| 1,2-diaminoethane | 0.86 | — | 545 | — | — |
| 1,3-diaminopropane | 0.85 | — | 165 | 230 | 480 |
| " | 1.28 | — | 130 | 200 | 260 |
| 1,6-diaminohexane | 0.86 | 120 | 190 | 230 | 400 |
| " | 1.29 | 120 | 260 | — | 360 |
| Triaminononane | 0.87 | 110 | 170 | 450 | 540 |
| " | 1.20 | 80 | — | — | — |
| " | 1.73 | 0 | — | — | — |
| Polypropylene oxide diamine[1] | 0.86 | — | — | 1400 | — |
| Methylene dianiline | 0.85 | — | 170 | — | — |
| " | 1.71 | — | 100 | >1200 | — |
| " | 3.40 | — | 70 | >1200 | — |
| Bis(aminophenoxyphenyl) propane | 0.86 | — | 130 | >1200 | — |
| Bis(aminophenoxyphenyl) propane | 1.72 | 70 | 100 | >1200 | — |
| Diethylene triamine | 1.05 | 80 | 90 | 225 | 420 |
| " | 1.21 | — | 65 | — | — |
| " | 1.58 | — | 40 | — | — |
| " | 2.10 | — | 0 | — | — |
| Triethylene tetramine | 1.13 | 100 | 100 | 120 | 220 |
| " | 1.20 | — | 85 | — | — |
| " | 2.27 | — | 0 | — | — |
| Tetraethylene pentamine | 1.23 | 70 | 85 | 90 | 100 |
| Tetraethylene pentamine | 1.85 | — | 0 | — | — |
| Pentaethylene hexamine | 1.07 | 90 | — | — | — |
| Pentaethylene hexamine | 1.14 | 85 | — | — | — |
| Pentaethylene hexamine | 1.29 | 80 | 80 | 90 | 100 |
| Pentaethylene hexamine | 1.94 | — | 0 | — | — |
| Polyethylene imine[2] | (2.56 wt. %) | — | 55 | — | 55 |

[1]Jeffaminem ™ D230 (Jefferson Chemical Co.)
[2]Corcat ™ P-18 (Virginia Chemicals Co.)
*R: ratio of amine groups to acid groups

EXAMPLE 5

This example serves to illustrate the preparation of dry resin-impregnated cloth and cured laminates according to this invention.

65 grams of the resin mixture of bismaleimide and maleamic acids prepared in Example 1 was added to a solution of 0.975 grams of triethylene tetramine in 35 grams of acetone. (The ratio of amine groups to acid groups was about 1.13). The solution was used to saturate glass cloth. The solution saturated cloth was placed in an air oven (180° C.) for about 5 minutes resulting in a dry resin-impregnated cloth (about 38 percent by weight resin). A laminate was prepared by placing 8 sheets of resin-impregnated cloth between two sheets of copper having a density of two ounces per square foot and heating in a press for 2 hours at about 180° C. and 3450 kPa (500 psi). The laminate was removed from the press and post cured at 220° C. for 24 hours.

The laminate was evaluated in accordance with the procedures of MIL-P-13949F and determined to have the following properties:

| | |
|---|---|
| Water Absorption (23° C., 24 hours) | 0.4% |
| Dielectric Constant (at $10^6$ cps) | 3.5 |
| Dissipation Factor (at $10^6$ cps) | 0.01 |

| -continued | |
|---|---|
| Copper Peel Strength | >60 kPa (9 psi) |

The laminate was also floated on molten solder (288° C.) for more than 10 minutes. The absence of blistering or delamination illustrate exceptional resistance to thermal stress.

EXAMPLE 6

This example serves to illustrate preferred embodiments of this invention where the properties of laminates are effected by the level of maleamic acid in mixtures of bismaleimides.

Laminates were prepared essentially as in Example 5 from materials indicated in Table 3. After the post cure at 220° C. the laminates were analyzed for visual signs of delamination as indicated by blisters, e.g. caused by steam generated from water liberated from ring closure of maleamic acids. As reported in Table 3, the laminate prepared from the bismaleimide resin having lower levels of maleamic acid had no visible blisters; the laminate prepared from the resin having higher levels of maleamic acid was severely blistered.

TABLE 3

| Bismaleimide Mixture (BMI/MIMA/BMA) | TETA[(1)] (g) | Blisters |
|---|---|---|
| 80/12/4 | 0.975 g | None |
| 41/34/10 | 1.65 g | Severe |

[(1)]TETA: triethylene tetramine

While specific embodiments of the invention have been described, it should be apparent to those skilled in the art that various modifications thereof can be made without departing from the true spirit and scope of the invention. Accordingly, it is intended that the following claims cover all such modifications within the inventive concept.

What is claimed is:

1. An actone-soluble bismaleimide composition comprising a mixture of at least one bismaleimide and a solubilizing amount of at least one maleamic acid, wherein said bismaleimides and maleamic acids are of the formula

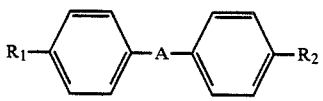

where A is —B—,

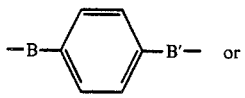 or

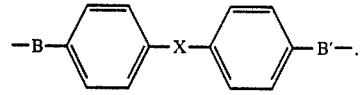

where B, B' and X are independently —O—, —SO$_2$—, —CO—, or

R$_3$ and R$_4$ being independently hydrogen, C$_1$–C$_3$ alkyl, or halogenated C$_1$–C$_3$ alkyl and n ranges from 0 to 6; and where R$_1$ and R$_2$ are independently the maleamic acid group, —NHCOCH=CHCOOH or the maleimide group,

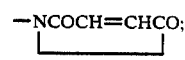

and wherein less than about 35% of the R1 and R2 groups are maleamic acid groups.

2. A composition according to claim 1 wherein A is

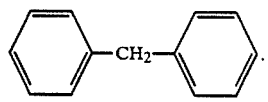

3. A composition according to claim 1 wherein said mixture of bismaleimides and maleamic acids is derived from bis(aminophenoxyphenyl) propane wherein between about 1 and 20% of the R$_1$ and R$_2$ groups are maleamic acid groups.

4. A composition according to claim 3 wherein between about 2 and 15% of the R$_1$ and R$_2$ groups are maleamic acid groups.

5. A solution comprising the composition of claim 4.

6. A solution according to claim 5 comprising at least about 40 percent by weight of said mixture.

7. A solution according to claim 6 comprising solvent selected from the group consisting of acetone, methyl ethyl ketone, methyl isobutyl ketone, tetrahydrofuran, dimethyl formamide, dimethyl actamide, dimethyl sulfoxide, N-methyl pyrrolidone, ethylene dichloride, toluene and xylene, and mixtures thereof.

8. A solution according to claim 7 where said solvent comprises acetone.

9. A solution according to claim 7 further comprising a species capable of interacting with maleamic acid groups 10. A solution comprising the composition of claim 2.

11. A solution according to claim 10 comprising a solvent selected from the group consisting of acetone, methyl ethyl ketone, methyl isobutyl ketone, tetrahydrofuran, dimethyl formamide, dimethyl acetamide, dimethyl sulfoxide, N-methyl pyrrolidone, ethylene dichloride, toluene and xylene, and mixtures thereof.

* * * * *